(12) United States Patent
Mitchell

(10) Patent No.: US 10,828,286 B2
(45) Date of Patent: Nov. 10, 2020

(54) NIACIN AND BERBERINE COMPOSITIONS AND METHODS OF USE THEREOF

(71) Applicant: GM Pharmaceuticals, Inc., Arlington, TX (US)

(72) Inventor: Odes W. Mitchell, Arlington, TX (US)

(73) Assignee: GM Pharmaceuticals, Inc., Arlington, TX (US)

( * ) Notice: Subject to any disclaimer, the term of this patent is extended or adjusted under 35 U.S.C. 154(b) by 0 days.

(21) Appl. No.: 16/420,048

(22) Filed: May 22, 2019

(65) Prior Publication Data

US 2019/0358211 A1 Nov. 28, 2019

Related U.S. Application Data

(60) Provisional application No. 62/676,155, filed on May 24, 2018.

(51) Int. Cl.
| | | |
|---|---|---|
| *A61K 31/4375* | (2006.01) | |
| *A61K 31/455* | (2006.01) | |
| *A61K 31/695* | (2006.01) | |
| *A61K 31/732* | (2006.01) | |
| *A61K 9/00* | (2006.01) | |

(52) U.S. Cl.
CPC ........ *A61K 31/4375* (2013.01); *A61K 9/0053* (2013.01); *A61K 31/455* (2013.01); *A61K 31/695* (2013.01); *A61K 31/732* (2013.01)

(58) Field of Classification Search
CPC .................................................. A61K 31/4375
USPC .......................................................... 514/300
See application file for complete search history.

(56) References Cited

U.S. PATENT DOCUMENTS

| | | | | |
|---|---|---|---|---|
| 9,018,193 | B2 * | 4/2015 | Reed | A61K 9/06 514/165 |
| 9,278,070 | B2 * | 3/2016 | Coulter | A61K 47/10 |
| 9,999,651 | B2 * | 6/2018 | Coulter | A61K 9/107 |

OTHER PUBLICATIONS

Caliceti, Current Medicinal Chemistry, 2016, 23, 1460-1476.*
Bruckert, Atherosclerosis 210 (2010) 353-361.*

* cited by examiner

*Primary Examiner* — Nizal S Chandrakumar
(74) *Attorney, Agent, or Firm* — Winstead PC

(57) ABSTRACT

In some embodiments, the present disclosure pertains to a composition including niacin up to about 1000 mg and berberine up to about 800 mg. In some embodiments, the niacin is in an amount of about 500 mg and the berberine is in an amount of about 100 mg. In some embodiments, the present disclosure pertains to a method that includes administering a composition to a subject in need thereof, where the composition includes niacin up to about 1000 mg and berberine up to about 800 mg. In some embodiments, the niacin is in an amount of about 500 mg and the berberine is in an amount of about 100 mg.

16 Claims, No Drawings

NIACIN AND BERBERINE COMPOSITIONS AND METHODS OF USE THEREOF

CROSS-REFERENCE TO RELATED APPLICATIONS

This patent application claims priority from, and incorporates by reference the entire disclosure of, U.S. Provisional Patent Application No. 62/676,155 filed on May 24, 2018.

TECHNICAL FIELD

The present disclosure relates generally to niacin and berberine and more particularly, but not by way of limitation, to niacin and berberine compositions and methods of use thereof.

BACKGROUND

This section provides background information to facilitate a better understanding of the various aspects of the disclosure. It should be understood that the statements in this section of this document are to be read in this light, and not as admissions of prior art.

Cardiovascular disease refers to several types of conditions affecting the heart and blood vessels (i.e., the circulatory system). Among the cardiovascular diseases, some of the more prevalent diseases and conditions include heart disease, stroke, and hypertension.

While cardiovascular disease affects people of all ages, ethnicities, and backgrounds, there are certain chronic conditions and lifestyle factors that put certain individuals at a higher risk. For example, high blood pressure, diabetes, and high levels of low-density lipoprotein (often referred to as "bad cholesterol"), are among some of the risk factors for cardiovascular disease. In addition, unhealthy behaviors such as tobacco use, poor diet, physical inactivity, obesity, and alcohol abuse can contribute to high blood pressure, heart disease, and other cardiovascular conditions. In particular cases, individuals with a family history of cardiovascular disease share common environments and risk factors that increase the likelihood of having a heart attack or stroke. In conjunction with those genetic factors, unhealthy lifestyle choices substantially increase the risk of cardiovascular disease for those individuals.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In some embodiments, the present disclosure pertains to a composition including niacin up to about 1000 mg and berberine up to about 800 mg. In some embodiments, the niacin is in a range of about 250 mg to about 1000 mg and the berberine is in a range of about 50 mg to about 800 mg. In some embodiments, the niacin is in a range of about 250 mg to about 1000 mg and the berberine is in a range of about 50 mg to about 300 mg. In some embodiments, the niacin is in a range of about 250 mg to about 1000 mg and the berberine is in a range of about 50 mg to about 200 mg. In some embodiments, the niacin is in a range of about 250 mg to about 750 mg and the berberine is in a range of about 50 mg to about 150 mg.

In some embodiments, the niacin is in an amount of about 1000 mg and the berberine is in an amount of about 200 mg. In some embodiments, the niacin is in an amount of about 750 mg and the berberine is in an amount of about 150 mg. In some embodiments, the niacin is in an amount of about 500 mg and the berberine is in an amount of about 100 mg. In some embodiments, the niacin is in an amount of about 250 mg and the berberine is in an amount of about 50 mg.

In some embodiments, the composition further includes pectin in an amount of about 40% by total weight of the composition. In some embodiments, the composition further includes silicon dioxide in a range of about 2.63 mg to about 7.89 mg and magnesium stearate in a range of about 3.25 mg to about 9.75 mg. In some embodiments, the silicon dioxide is about 5.26 mg and the magnesium stearate is about 6.5 mg. In some embodiments, the composition is administered orally via a tablet or capsule. In some embodiments, the tablet or capsule utilizes a modified-release mechanism, including, but not limited to, delayed-release mechanisms, extended-release mechanisms, targeted-release mechanisms, sustained-release mechanisms, controlled-release mechanisms, or combinations thereof.

In some embodiments, the present disclosure pertains to a method that includes administering a composition to a subject in need thereof, where the composition includes niacin up to about 1000 mg and berberine up to about 800 mg. In some embodiments, the niacin is in an amount of about 500 mg and the berberine is in an amount of about 100 mg. In some embodiments, the composition further includes pectin in an amount of about 40% by total weight of the composition. In some embodiments, the composition further includes silicon dioxide in a range of about 2.63 mg to about 7.89 mg and magnesium stearate in a range of about 3.25 mg to about 9.75 mg. In some embodiments, the composition is administered orally via a tablet or capsule. In some embodiments, the tablet or capsule utilizes a modified-release mechanism, including, but not limited to, delayed-release mechanisms, extended-release mechanisms, targeted-release mechanisms, sustained-release mechanisms, controlled-release mechanisms, or combinations thereof.

DETAILED DESCRIPTION

In various embodiments, the present disclosure is directed to a composition for oral administration to promote cardiovascular health and prevent cardiovascular disease or reoccurrence of cardiovascular events. The compositions disclosed herein include a combination of niacin and berberine that were specifically chosen and combined according to their biological and physiological activities. Each component can be used in combination, or singularly, to significantly improve cardiovascular health. Described herein are advanced formulas for the modified-release of niacin and berberine into the bloodstream. In various embodiments, the composition disclosed herein can utilize various modified-release mechanisms, for example, delayed-release mechanisms, extended-release mechanisms, targeted-release mechanisms, sustained-release mechanisms, controlled-release mechanisms, or combinations thereof, to control the release of the composition into the bloodstream. In a particular embodiment, the present disclosure utilizes an extended-release mechanism to control the release of the composition into the bloodstream.

Nicotinic acid, or niacin, is one of the eight B-complex vitamins. Niacin has a wide range of uses in the body, helping functions in the digestive system, skin, nervous system, and the circulatory system. In particular, studies have shown that niacin improves blood lipids and reduces the risk of atherosclerotic cardiovascular disease (i.e., atherosclerosis).

Atherosclerosis is caused by a complex interplay between lipoproteins, white blood cells, the immune system, and the natural elements of the arterial wall. Atherosclerosis leads to the formation of lesions, or plaques, that protrude into the lumen of an artery causing arterial narrowing, which can disturb blood flow. A rupture of atherosclerotic plaque may lead to thrombosis, causing a sudden disruption of blood flow in the artery. Studies have indicated that the lipid-lowering effects of niacin are accompanied by a regression of atherosclerosis.

Studies have further indicated that niacin inhibits the production of very-low-density lipoprotein (VLDL) in the liver and subsequently its metabolite, low-density lipoprotein (LDL). VLDL transports both triglycerides and cholesterol, and, once in circulation, VLDL is broken down in capillary beds, releasing triglycerides for energy utilization from cells or storage in adipose tissue. After triglycerides are released from VLDL, its composition changes, and it becomes intermediate-density lipoprotein (IDL). In time, when the amount of cholesterol increases, IDL become low-density lipoprotein (LDL).

When the body has too much LDL cholesterol, the LDL cholesterol can build up on the walls of blood vessels, this buildup is also known as plaque. As blood vessels build up plaque over time, the insides of the vessels narrow, and this in turn, blocks blood flow to and from the heart and other organs. When blood flow to the heart is blocked, it can cause angina or a heart attack.

Studies show that niacin raises high-density lipoprotein (HDL) cholesterol by causing a reduction of cholesterol transfer from HDL to VLDL and delays the clearance of HDL. HDL absorbs cholesterol and carries it back to the liver, where the liver then flushes it from the body. As a result, high levels of HDL cholesterol can lower the risk for heart disease and stroke. Niacin has been shown to lower total cholesterol, LDL cholesterol, triglycerides, and lipoprotein, while also increasing HDL cholesterol levels. These effects promote healthy cholesterol levels, and specifically promote healthy cardiovascular systems.

Furthermore, studies indicate that niacin plays an important role in the reduction of inflammation and production of histamine, a chemical compound capable of dilating blood vessels and improving circulation. This can be especially advantageous for individuals who have already suffered from cardiac arrest or heart disease, including previously having had a heart attack. Due to the lipid-lowering effects and the production of histamine, niacin can help to lower the risk of a reoccurrence of a cardiac event from taking place.

In addition to niacin, studies indicate that berberine has a favorable effect on triglycerides and cholesterol levels, and has been shown to reduce apolipoprotein B, the primary apolipoprotein of chylomicrons, VLDL, IDL, and LDL particles, which carries lipids, including cholesterol, around the body. As such, berberine helps to keep cholesterol levels within healthy ranges. Berberine can help facilitate healthy levels of LDL cholesterol, for example, by facilitating healthy ranges of LDL particle numbers and small density LDL. Thus, berberine has been shown to have the ability to help maintain healthy cholesterol levels thereby decreasing the risk of cardiovascular diseases caused by unhealthy levels of cholesterol.

Berberine is a quaternary ammonium salt from the protoberberine group of benzylisoquinoline alkaloids found in certain plants, for example, *Berberis*. A major key focus on cardiovascular health is healthy blood sugar levels, and berberine has been shown to be effective at keeping blood sugar levels healthy. In regard to the effect of berberine regulating blood sugar levels, it has been shown that berberine works by a variety of different mechanisms. Studies indicate that berberine can decrease insulin resistance, making the blood sugar lowering hormone insulin more effective, and berberine can increase glycolysis, helping break down sugar inside cells. Studies have also indicated that berberine can decrease sugar production in the liver and slow the breakdown of carbohydrates in the body which can help maintain lower blood sugar levels.

Studies have also indicated that berberine is able to activate the adenosine monophosphate-activated protein kinase (AMPK) enzyme while inhibiting protein-tyrosine phosphatase 1B (PTP1B). Activating AMPK has been show to play a key role in reversing insulin resistance, promoting glycolysis, and reducing oxidative stress. One result of activating AMPK is suppression of hepatic glucose output, so that insulin and insulin-like growth factor 1 (IGF-1) levels are lower. The AMPK activation by berberine also stimulates the release of nitric oxide, a signaling molecule that relaxes the arteries, increases blood flow and lowers blood pressure, protects against atherosclerosis, and can dilate blood vessels. Moreover, PTP1B plays an important role in the negative regulation of insulin signal transduction pathways, and it has been shown that PTP1B inhibitors enhance the sensibility of insulin receptors and have advantageous curing effect for insulin resistance related diseases.

Furthermore, studies indicate that berberine has the ability to help regulate the expression of proprotein convertase subtilisin/kexin type 9 (PCSK9). Studies have identified the higher the PCSK9 levels, the higher the risk of atherosclerosis, fasting plasma glucose, and insulin resistance. Inhibiting PCSK9 can reduce the amount of harmful LDL cholesterol circulating in the bloodstream, and lower LDL levels result in healthier arteries and fewer heart attacks, strokes, and other problems related to cholesterol-clogged arteries.

In view of the aforementioned biological and physiological properties of niacin and berberine, disclosed herein, are compositions that provide optimal amounts of niacin and berberine to meet the unique requirements to promote cardiovascular health by lowering LDL cholesterol, triglycerides, and lipoprotein, while increasing HDL cholesterol levels, and maintaining healthy blood sugar levels. A particular example of active ingredients and amounts thereof within a composition will be described in more detail below with respect to Table 1. In some embodiments, the example disclosed in Table 1 can be adapted for modified-release usage, such as, but not limited to, extended-release usage.

Amounts are given based on a single dosage and, as will be appreciated by those of ordinary skill in the art, "mg" refers to milligrams. In some embodiments, the daily amount can be up to 2 modified-release doses per day. Additional embodiments allow for higher or lower doses per serving and more or less than 2 modified-release doses per day. In certain embodiments, the dosing can be lower, for example, in an immediate-release tablet or capsule. In some embodiments, the doses can be higher, for example, in a delayed-release tablet or capsule, an extended-release tablet or capsule, a targeted-release tablet or capsule, a sustained-release tablet or capsule, or a controlled-release tablet or capsule.

Table 1 below illustrates an example of a composition according to an aspect of the present disclosure. In this particular example, the composition includes active ingredients, such as, niacin in an amount of about 500 mg and berberine in an amount of about 100 mg within a pharmaceutically acceptable carrier capable of modified-release. In some embodiments, the composition includes inactive ingredients, for example, silicon dioxide, magnesium stearate, or other excipients. In a particular embodiment, the inactive ingredients include, for example, silicon dioxide in an amount of about 5.26 mg and magnesium stearate in an amount of about 6.5 mg. In various embodiments, pectin can be utilized in the composition in an amount of about 40% by total weight of the composition to facilitate in a modified-release of the composition, for example, an extended-release.

TABLE 1

| Active Ingredients | Amount |
|---|---|
| Niacin (B$_3$) | 500 mg |
| Berberine | 100 mg |

In some embodiments, the composition includes niacin up to about 1000 mg and berberine up to about 800 mg within a pharmaceutically acceptable carrier capable of modified-release. In some embodiments, the composition includes niacin in a range of about 250 mg to about 1000 mg and berberine in a range of about 50 mg to about 800 mg within a pharmaceutically acceptable carrier capable of modified-release. In some embodiments, the composition includes niacin in a range of about 250 mg to about 1000 mg and berberine in a range of about 50 mg to about 300 mg within a pharmaceutically acceptable carrier capable of modified-release.

In various embodiments, the composition includes active ingredients in an amount of about 0.5 to 2 times that indicated in Table 1, for example, niacin in a range of about 250 mg to about 1000 mg and berberine in a range of about 50 mg to about 200 mg within a pharmaceutically acceptable carrier capable of modified-release. In some embodiments, the composition includes niacin in a range of about 250 mg to about 750 mg and berberine in a range of about 50 mg to about 150 mg within a pharmaceutically acceptable carrier capable of modified-release.

In some embodiments, the composition includes niacin in an amount of about 1000 mg and berberine in an amount of about 200 mg within a pharmaceutically acceptable carrier capable of modified-release. In some embodiments, the composition includes niacin in an amount of about 750 mg and berberine in an amount of about 150 mg within a pharmaceutically acceptable carrier capable of modified-release. In some embodiments, the composition includes niacin in an amount of about 500 mg and berberine in an amount of about 100 mg within a pharmaceutically acceptable carrier capable of modified-release. In some embodiments, the composition includes niacin in an amount of about 250 mg and berberine in an amount of about 50 mg within a pharmaceutically acceptable carrier capable of modified-release.

In some embodiments, the niacin is in an amount up to 1000 mg. In some embodiments, the niacin is in a range of about 250 mg to about 750 mg. In some embodiments, the niacin is in a range of about 250 mg to about 1000 mg. In certain embodiments, the niacin is about 250 mg. In other embodiments, the niacin is about 500 mg. In some embodiments, the niacin is about 750 mg. In certain embodiments, the niacin is about 1000 mg.

In some embodiments, the berberine is in an amount up to about 800 mg. In some embodiments, the berberine is in a range of about 50 mg to about 150 mg. In some embodiments, the berberine is in a range of about 50 mg to about 200 mg. In some embodiments, the berberine is in a range of about 50 mg to about 300 mg. In some embodiments, the berberine is in a range of about 50 mg to about 800 mg. In some embodiments, the berberine is about 50 mg. In some embodiments, the berberine is about 100 mg. In some embodiments, the berberine is about 150 mg. In some embodiments, the berberine is about 200 mg. In some embodiments, the berberine is about 250 mg. In some embodiments, the berberine is about 300 mg. In some embodiments, the berberine is about 350 mg. In some embodiments, the berberine is about 400 mg. In some embodiments, the berberine is about 450 mg. In some embodiments, the berberine is about 500 mg. In some embodiments, the berberine is about 550 mg. In some embodiments, the berberine is about 600 mg. In some embodiments, the berberine is about 650 mg. In some embodiments, the berberine is about 700 mg. In some embodiments, the berberine is about 750 mg. In some embodiments, the berberine is about 800 mg.

In some embodiments, the present disclosure relates to a method of promoting cardiovascular health. In some embodiments, the method includes administering one or more of the compositions described herein to a subject in need thereof. For example, in some embodiments, the method includes administering a composition to a subject in need thereof, where the composition includes up to about 1000 mg of niacin and up to about 800 mg of berberine. In some embodiments, the method includes administering a composition to a subject in need thereof, where the composition includes about 250 mg to about 1000 mg of niacin and about 50 mg to about 800 mg of berberine. In some embodiments, the method includes administering a composition to a subject in need thereof, where the composition includes about 250 mg to about 1000 mg of niacin and about 50 mg to about 300 mg of berberine.

In some embodiments, the method includes administering a composition to a subject in need thereof, where the composition includes about 250 mg to about 1000 mg of niacin and about 50 mg to about 200 mg of berberine. In some embodiments, the method includes administering a composition to a subject in need thereof, where the composition includes about 250 mg to about 750 mg of niacin and about 50 mg to about 150 mg of berberine.

In some embodiments, the method includes administering a composition to a subject in need thereof, where the composition includes about 250 mg of niacin and about 50 mg of berberine. In some embodiments, the method includes administering a composition to a subject in need thereof, where the composition includes about 500 mg of niacin and about 100 mg of berberine. In some embodiments, the method includes administering a composition to a subject in need thereof, where the composition includes about 750 mg of niacin and about 150 mg of berberine. In some embodiments, the method includes administering a composition to a subject in need thereof, where the composition includes about 1000 mg of niacin and about 200 mg of berberine.

In some embodiments, the compositions disclosed herein can be administered orally via, for example, a tablet or capsule. In some embodiments, the administering includes orally administering the compositions as disclosed herein via the tablet or capsule. In some embodiments, the tablet or capsule can utilize a modified-release mechanism, as discussed in further detail herein. In some embodiments, the modified-release mechanism is an extended-release mechanism. In some embodiments, the administering occurs daily. In some embodiments, the administering occurs 2 times a day. In some embodiments, the administering occurs up to 4 times a day. In some embodiments, the administering occurs 2 to 4 times a day. In some embodiments, the administering occurs 3 to 4 times a day. In some embodiments, the administering occurs more than 4 times a day.

In various embodiments, the compositions disclosed herein can utilize various modified-release mechanisms, such as, but not limited to, delayed-release mechanisms, extended-release mechanisms, targeted-release mechanisms, sustained-release mechanisms, controlled-release mechanisms, or combinations thereof, to control the release of the composition into the bloodstream.

In various embodiments, the modified-release can be a mechanism that delivers a dosage of the composition with a delay after its administration (delayed-release). In other embodiments, the modified-release can be a mechanism that delivers a dosage of the composition for a prolonged period of time (extended-release). In certain embodiments, the modified release can be a mechanism that delivers a dosage of the composition to a specific target in the body (targeted-release).

In some embodiments, the modified-release can be a sustained-release mechanism that is designed to liberate, or release, the composition at a predetermined rate in order to maintain a constant concentration for a specific period of time with minimum side effects. In certain embodiments, this can be achieved through a variety of formulations, including, but not limited to, liposomes and drug-polymer conjugates, for example, hydrogels and the like. In certain embodiments, sustained-release can be construed as a form of "controlled-release" rather than strictly "sustained".

In some embodiments, the modified-release can be a controlled-release mechanism that is designed to maintain the composition release over a sustained period at a nearly constant rate. In some embodiments, the modified-release can be a sustained-release mechanism that is designed to maintain the composition release over a sustained period, but not necessarily at a constant rate.

In various embodiments, pectin can be included in the composition in an amount of about 40% by total weight of the composition. In some embodiments, the pectin can be utilized to facilitate in the extended-release of the composition. In some embodiments, about 40% pectin by total weight of the composition can facilitate in the extended-release of the active ingredients by up to about 9 hours. In some embodiments, the pectin can be in utilized to facilitate in the release of the composition into the bloodstream for a duration from about 1 hour to about 20 hours.

In some embodiments, pectin can be in an amount capable of 92% to 100% release of the composition at approximately 20 hours. In some embodiments, pectin can be in an amount capable of 84% to 93% release of the composition at approximately 12 hours. In some embodiments, pectin can be in an amount capable of 71% to 82% release of the composition at approximately 9 hours. In some embodiments, pectin can be in an amount capable of 52% to 65% release of the composition at approximately 6 hours. In some embodiments, pectin can be in an amount capable of 28% to 39% release of the composition at approximately 3 hours. In some embodiments, pectin can be in an amount capable of 9% to 14% release of the composition at approximately 1 hour. In some embodiments, higher amounts of pectin by total weight of the composition can change the dissolution rate of the composition at particular time intervals. For example, in some embodiments, when the pectin is in a higher formulation, the percent of release of the composition can be less than the percent release of the composition at a longer time (e.g. 20 hours) for a composition with less pectin by total weight of the composition. Similarly, in some embodiments, when the pectin is in a higher formulation, the percent of release of the composition can be higher than the percent release of the composition at a shorter time (e.g. 3 hours) for a composition with less pectin by total weight of the composition.

In various embodiments, modified-release mechanisms and its variants are mechanisms used in tablets or capsules to dissolve a composition over time in order to be released slower and steadier into the bloodstream while having the advantage of being taken at less frequent intervals than immediate-release formulations of the same composition. In addition to tablets or capsules, and, for example, injectable drug carriers, in certain embodiments, forms of controlled-release compositions include, but are not limited to, gels, implants and devices, and transdermal patches.

In additional embodiments, the compositions of the present disclosure can be in the form of an immediate-release formulation rather than a modified-release formulation. As such, in some embodiments, the compositions disclosed herein can be utilized with or without a modified-release mechanism, a pharmaceutically acceptable carrier, or a pharmaceutically acceptable carrier capable of modified-release. In some embodiments, the compositions disclosed herein can utilize, for example, an immediate-release mechanism for the delivery of the composition into the bloodstream.

In some embodiments, the composition includes inactive ingredients, for example, silicon dioxide, magnesium stearate, or other excipients. In some embodiments, the compositions of the present disclosure include about 2.63 mg to about 7.89 mg of silicon dioxide. In some embodiments, the compositions include about 3.25 mg to about 9.75 mg of magnesium stearate. In some embodiments, the silicon dioxide is in an amount of about 5.26 mg. In some embodiments, the magnesium stearate is in an amount of about 6.5 mg. In some embodiments, the composition can include other excipients, such as, but not limited to, anti-adherents, binders, coatings, colors, disintegrants, flavors, glidants, lubricants, preservatives, sorbents, sweeteners, vehicles, or combinations thereof.

Although various embodiments of the present disclosure have been described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A composition comprising:
    niacin up to 1000 mg;
    berberine up to 800 mg; and
        pectin in an amount of 40% by total weight of the composition to facilitate in extended-release of the niacin and the berberine by up to 9 hours.

2. The composition of claim 1, wherein the niacin is in a range of 250 mg to 1000 mg and the berberine is in a range of 50 mg to 800 mg.

3. The composition of claim 1, wherein the niacin is in a range of 250 mg to 1000 mg and the berberine is in a range of 50 mg to 300 mg.

4. The composition of claim 1, wherein the niacin is in a range of 250 mg to 1000 mg and the berberine is in a range of 50 mg to 200 mg.

5. The composition of claim 1, wherein the niacin is in a range of 250 mg to 750 mg and the berberine is in a range of 50 mg to 150 mg.

6. The composition of claim 1, wherein the niacin is in an amount of 1000 mg and the berberine is in an amount of 200 mg.

7. The composition of claim 1, wherein the niacin is in an amount of 750 mg and the berberine is in an amount of 150 mg.

8. The composition of claim 1, wherein the niacin is in an amount of 500 mg and the berberine is in an amount of 100 mg.

9. The composition of claim 1, wherein the niacin is in an amount of 250 mg and the berberine is in an amount of 50 mg.

10. The composition of claim 1, comprising:
    silicon dioxide in a range of 2.63 mg to 7.89 mg; and
    magnesium stearate in a range of 3.25 mg to 9.75 mg.

11. The composition of claim 10, wherein the silicon dioxide is 5.26 mg and the magnesium stearate is 6.5 mg.

12. The composition of claim 1, wherein the composition is administered orally via a tablet or capsule.

13. A method comprising:
    administering a composition to a subject in need thereof, wherein the composition comprises:
        niacin up to 1000 mg;
        berberine up to 800 mg; and
pectin in an amount of 40% by total weight of the composition to facilitate in the release of the niacin and the berberine in the subject for a duration from 1 hour to 20 hours.

14. The method of claim 13, wherein the niacin is in an amount of 500 mg and the berberine is in an amount of 100 mg.

15. The method of claim 13, wherein the composition comprises:
    silicon dioxide in a range of 2.63 mg to 7.89 mg; and
    magnesium stearate in a range of 3.25 mg to 9.75 mg.

16. The method of claim 13, wherein the composition is administered orally via a tablet or capsule.

* * * * *